(12) United States Patent
Okerlund et al.

(10) Patent No.: US 7,027,855 B2
(45) Date of Patent: Apr. 11, 2006

(54) R-PEAK DETECTION CORRECTIONS FOR IMPROVED CARDIAC GATED RECONSTRUCTION

(75) Inventors: Darin Okerlund, Muskego, WI (US); Tinsu Pan, Brookfield, WI (US); Mark E. Woodford, Waukesha, WI (US); Kishore C. Acharya, Brookfield, WI (US)

(73) Assignee: General Electric Company, NY (US)

( * ) Notice: Subject to any disclaimer, the term of this patent is extended or adjusted under 35 U.S.C. 154(b) by 250 days.

(21) Appl. No.: 10/064,899

(22) Filed: Aug. 27, 2002

(65) Prior Publication Data

US 2004/0042581 A1    Mar. 4, 2004

(51) Int. Cl.
 *A61B 5/04* (2006.01)
(52) U.S. Cl. .................................... 600/509
(58) Field of Classification Search ............ 600/407, 600/425, 509, 516, 521; 607/23
See application file for complete search history.

(56) References Cited

U.S. PATENT DOCUMENTS

| 5,503,159 | A  | * | 4/1996 | Burton ...................... 600/516 |
| 6,708,055 | B1 | * | 3/2004 | Geiser et al. ............... 600/425 |
| 6,738,667 | B1 | * | 5/2004 | Deno et al. .................. 607/23 |

* cited by examiner

*Primary Examiner*—George Manuel
(74) *Attorney, Agent, or Firm*—Quarles & Brady LLP; Carl Horton

(57) ABSTRACT

A method and apparatus for use with a gated CT imaging system for correcting for Rpeak errors in a heart beat signal, the method including identifying heart rate corresponding to each specific heart beating cycle and comparing the heart rate for each specific cycle to moving averages to determine when a likely Rpeak error has occurred and, when a likely error has occurred, modifying the heart beat signal to generate a more accurate signal and thereby render more accurate gated images.

18 Claims, 5 Drawing Sheets

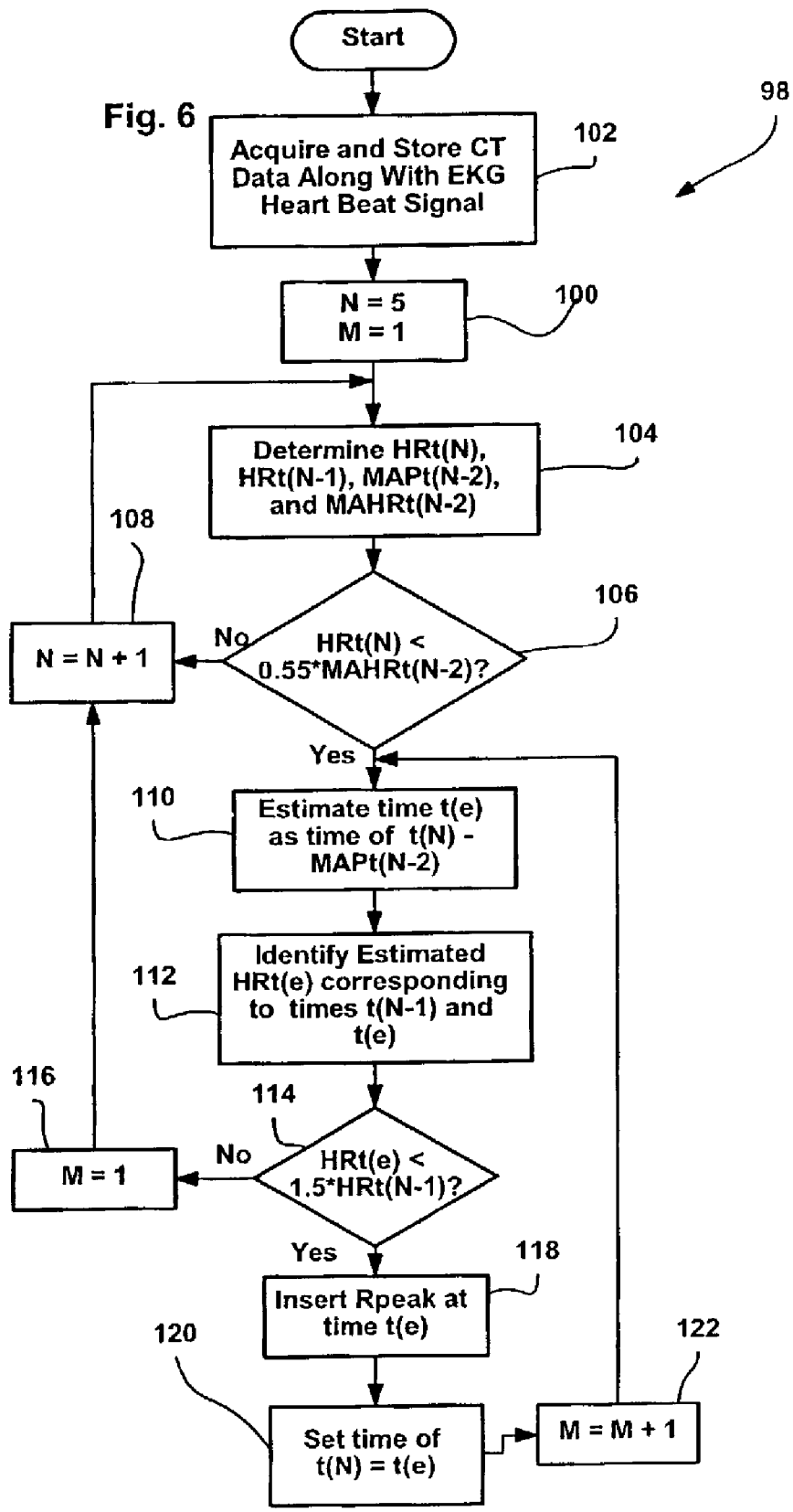

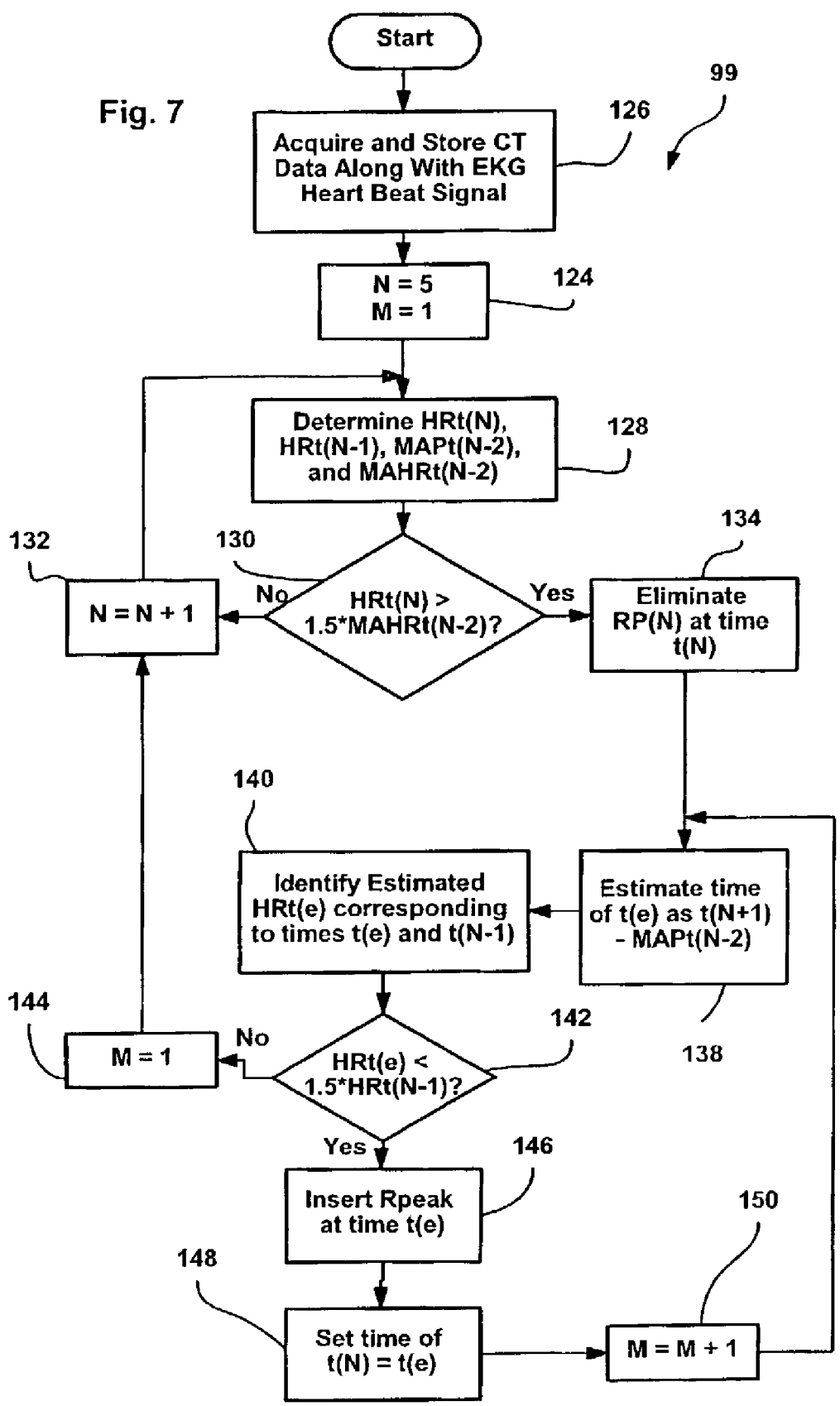

R-PEAK DETECTION CORRECTIONS FOR IMPROVED CARDIAC GATED RECONSTRUCTION

BACKGROUND OF INVENTION

The field of the invention is gated computerized tomography (CT) imaging and more specifically methods and apparatus that correct for missed R-peak detections, erroneously identified R-peak detections and shifted R-peak detections.

Many different types of medical imaging systems have been developed that are used for different purposes. Perhaps the most common type of imaging system category includes X-ray systems wherein radiation is directed across a portion of a patient to be imaged and toward a detector panel. An exemplary X-ray detector panel includes a CsI scintillator coupled with an amorphous silicon array. With radiation directed toward a region of a patient to be images (i.e., a region of interest), the region of interest blocks some of the radiation and some of the radiation passes through the region and is collected by the panel. The amount of radiation that passes through the region along the trajectory of a given radiation ray depends upon the type of tissue along the trajectory. Thus, a tumor may block more radiation than flesh and bone may block more radiation than a tumor and so on. Hence X-ray system can be used to collect a "projection" through a patient.

While useful, simple X-ray systems have many limitations. One important limitation to X-ray imaging systems is that such systems, as described above, only provide side projections through a region and cannot be used to generate other useful images such as "slice" images (i.e., images perpendicular to projection images) through a region of interest. For instance, an exemplary useful slice image may include a slice image through a patient's heart.

Another type of imaging system that is useful in generating slice images is generally referred to as a computerized tomography (CT) system. An exemplary CT system includes a radiation source and a radiation detector mounted on opposite sides of an imaging area where the imaging area is centered along a translation or Z-axis. The source generates radiation that is collimated into a beam including a plurality of radiation rays directed along trajectories generally across the imaging area. A line detector may be positioned perpendicular to the Z-axis to collect slice image data during a data acquisition period.

During an acquisition period a region of interest is positioned within the imaging area and, with the radiation source turned on, the region of interest blocks some of the radiation and some of the radiation passes through the region and is collected by the line detector. As in X-ray systems, the amount of radiation that passes through the region of interest along the trajectory of a given radiation ray is dependent upon the type of tissue along the trajectory. In CT systems the source and line detector are rotated about the region of interest within a rotation plane through the region of interest so that radiation "projections" can be collected for a large number of angles about the region. By combining the projections corresponding to a slice through the region of interest using a filtering and back projecting technique, a two-dimensional tomographic or axial image (i.e., a slice image) of the slice is generated.

While some diagnostic techniques only require one or a small number of slice images, many techniques require a large number of parallel CT slice images. For example, some techniques require examination of many parallel images to identify where an arterial blockage begins and ends and the nature of the blockage there between. As another example, many techniques reformat two dimensional data into, in effect, three dimensional volumetric images, that can be sliced and diced in several different directions so that various image planes can be employed. For instance, where two dimensional data is acquired for transverse or cross sectional slices through a three dimensional region of interest (e.g., through a patient's torso), the data may be reformatted to generate sagital (i.e., the side plane passing through the long axis of the body) or coronal (i.e., the frontal plane passing through the long axis of the body) images through the region of interest.

In order to generate several slice images rapidly, CT detectors are typically configured having several parallel detector rows such that, during a single rotation about the imaging area, each detector row collects data that can subsequently be used to generate a separate CT slice image.

While increasing the number of detector rows reduces acquisition time, detector elements are relatively expensive and thus more rows translates into a more costly overall system. As a balance between cost and speed, most multi-row detectors include less than 10 detector rows. Hereinafter it will be assumed that an exemplary detector includes eight detector rows.

Where a detector includes eight rows and more than eight slice images are required, several different acquisition periods are typically used to acquire the necessary slice image data. For instance, assume that 80 slice images (an admittedly small number but sufficient for exemplary purposes) through a ROI are required. In this case, the ROI may be divided into ten separate sub-volumes, each of the ten sub-volumes corresponding to a separate eight of the 80 required slice images. Thereafter, ten separate acquisition periods may be used to collect the sets of slice image data corresponding to the ten sub-volumes, data corresponding to eight separate slice images collected during each of the ten separate acquisition periods.

It has been found that, for large volumes or ROIs, data necessary to generate many parallel thin slice images can be acquired most rapidly by helically collecting the data. To this end, while the source and detector are rotated about the imaging area, a patient bed is translated there through so that the radiation fan beam sweeps a helical path through the ROI. After helical data is collected, the data is converted to slice image data by any of several different weighting and filtering processes and thereafter the slice image data is back projected to form the viewable image.

In the case of helically acquired and stored raw data, the data can be used to construct virtually any number of slice images through a corresponding ROI. For instance, despite using a detector having eight rows of elements to collect helical data, the data may be processed to generate 16, 20, 500 or even thousands of separate slice images or, indeed, may be interpolated to generate a 3-D volumetric image, if desired.

In most imaging systems that generate still images, it is important that, to the extent possible, during data acquisition, the structure being imaged remain completely still. Even slight structure movement during acquisition can cause image artifacts in, and substantially reduce the diagnostic value of, resulting images. For this reason, during acquisition periods, patients are typically instructed to maintain the region of interest within the imaging area as still as possible by, for instance, holding the patient's breadth.

Despite a patient's attempts to control movement, certain anatomical structures cannot be held still and continue movement during acquisition periods. For instance, a patient's heart beats continually during data acquisition cycles and the beating movement complicates the process of acquiring diagnostic quality data.

In the case of the heart, fortunately, the beating cycle is repetitive and there are certain cycle phases during which the heart muscle is relatively at rest. As well known in the art, during a diastolic phase of the beating cycle when the heart is filling with blood, the heart is relatively at rest and movement is minimal. Thus, by restricting data acquisition periods to the diastolic phases of the heart beating cycle, relatively movement-free data can be acquired and used to generate CT slice images.

To this end, the industry has developed cardiac gated CT imaging systems. These systems generally take two different forms including shoot and move gating scans and retro-gating reconstructions. In the case of shoot and move scans, an electrocardiogram (EKG) system is used to monitor heart beating phase and to gate the acquisition of data so that data is only acquired during specific phases of the heart beating cycle (e.g., systolic, diastolic, etc.) Thereafter, the acquired data is used to generate slice images in a conventional manner.

In the case of retro-gating reconstruction, a full set of helical data is acquired and stored along with corresponding EKG signals. Thereafter, a heart cycle phase range is selected which indicates a range of the cycle for which images should be generated and an image reconstructor retrieves the helical data sub-set corresponding to the phase range from each heart cycle and generates the required images. Hereinafter the phrase "phase location" will be used to refer to as a phase point within a heart cycle and the phrase "phase range" will be used to refer to a range that is centered on a corresponding phase location.

In addition to minimizing movement related image artifacts, each of the EKG-gating processes (i.e., prospective and retrospective) is also meant to reduce mis-registration between sets of images that are generated using data corresponding to different sub-volumes of a region of interest. For instance, in the case above where a region is divided into ten separate sub-volumes and data for each sub-volume is collected during a separate acquisition period, if data for two consecutive sub-volumes is collected during different heart beating phases (i.e., during different phased of the heart cycles corresponding to the two consecutive sub-volumes), resulting images will likely be misaligned. Thus, by collecting data for all sub-volumes during similar heart beating phases, misalignment is substantially reduced.

In the cases of axially acquired data and helically acquired data this means restricting data to a specified phase range within each heart beating cycle. For instance, the acquired period may be between 70% and 80% of the total heart beating cycle where the cycles begin and end at peak cycle amplitudes. Hereinafter peak cycle amplitudes will be referred to as R-peaks and a heart beating cycle between two R-peaks will be referred to as an R-to-R interval.

Because EKG-gated reconstruction techniques are based on the cardiac R-to-R interval, it is critical that R-peak instances be precisely and accurately identified for each heart cycle. In practice, unfortunately, there are several sources of R-peak error in typical CT imaging systems that use gated techniques. For instance, patient arrhythmia such as premature ventricular contraction (PVC) has been known to throw off R-peak detection. As another instance, EKG line noise in some systems is appreciable and can cause R-peak errors. Moreover, the R-peak detection circuitry often has inherent limitations that result in R-peak errors.

R-peak detection errors have several consequences. For instance, when a heart beat occurs but an R-peak is not recorded, projection data corresponding to the missed heart cycle will not be available to generate an image at a corresponding selected location in space and time. As another instance, when an R-peak is recorded but does not correspond to an actual heart beat or is shifted in time with respect to a corresponding heart beat (i.e., an artificial R-peak), the phase location of an image generated using data corresponding to the artificial R-peak will be inaccurate. These R-peak errors cause discontinuities in the image series which are readily apparent in a coronal or a sagital view from a multi-planar reformat rendering.

SUMMARY OF INVENTION

It has been recognized that when a patient is at rest during data acquisition, the patient's heart beat is typically repetitive and periodic. Thus, when an EKG signal is acquired for use in gated CT imaging, if a patient is at rest when the signal is acquired, the signal should also be repetitive and periodic. For this reason, whenever one or more EKG signal cycles are appreciably irregular, it is likely that an EKG signal acquisition or recording error has occurred (i.e., either a signal Rpeak has been missed, artificially recorded or prematurely recorded). Thus, by identifying EKG signal irregularities and tracking the repetitive and periodic moving averages of the EKG signal, the moving averages can be used to correct the irregularities and therefore render all of the CT data useful.

Consistent with the above discussion, the present invention includes a method to be used with a CT imaging system including a heart beat monitor that senses R-peaks and generates a heart beat signal including R-peak pulses where each R-peak pulse indicates a sensed peak heart cycle magnitude, the method for correcting for heart beat signal errors corresponding to data collected over the course of several heart cycles, the method comprising the steps of, for each specific heart cycle where the specific heart cycle corresponds to a period between first and second R-peak pulses occurring at times $t(1)$ and $t(2)$, respectively: identifying a heart rate, using the heart rate to determine when an R-peak error has likely occurred and, when an R-peak error has likely occurred, modifying the EKG signal Rpeak pulse times.

In some embodiments the step of using includes the step of determining when at least one undetected R-peak has likely occurred between times $t(1)$ and $t(2)$ and where the step of modifying includes, when at least one undetected R-peak has likely occurred, storing at least one estimated R-peak pulse time $t(e)$ corresponding to the EKG signal between times $t(1)$ and $t(2)$.

More specifically, wherein preceding cycles are heart cycles that precede the specific heart cycle, the step of using may further include the steps of identifying a moving average rate corresponding to the moving average heart rate of a sub-set of the preceding cycles and determining that at least one undetected R-peak pulse has likely occurred between times $t(1)$ and $t(2)$ when the heart rate is less than Y % of the moving average rate.

Even more specifically, the method may further include the step of identifying a moving average period corresponding to the moving average heart cycle period of a sub-set of the preceding cycles and the step of determining may further include the steps of identifying a preceding heart rate corresponding to at least one preceding heart cycle, identifying the estimated R-peak time $t(e)$ as the time that precedes time t(2) by the moving average period, identifying an estimated heart rate corresponding to times t(e) and t(1) and determining that at least one undetected R-peak pulse has likely occurred between times t(1) and t(2) when the estimated heart rate is less than Z times the preceding heart rate.

In at least some embodiments the method further includes the step of (a) determining when at least another undetected R-peak has likely occurred between times t(1) and t(2) and (b) when at least another undetected R-peak has likely occurred, storing another estimated R-peak pulse time corresponding to the EKG signal between times t(e) and t(1). Here the method may further include repeating steps (a) and (b) until it is unlikely that another undetected R-peak pulse has occurred between times t(1) and t(2) IN some embodiments the step of determining when at least another undetected R-peak has likely occurred further includes the steps of identifying the next estimated R-peak time as the time that precedes the previous R-peak time corresponding to the most recently stored estimated R-peak pulse time by the moving average period, identifying an estimated heart rate corresponding to the next estimated and previous R-peak times and determining that at least another R-peak pulse has likely occurred between times t(1) and t(2) when the estimated heart rate is less than Z times the preceding heart rate.

In some embodiments the moving average rate is the average corresponding to the heart cycles that precede the specific heart cycle by four cycles, three cycles and two cycles and Y is 55. Also, the moving average heart cycle period may correspond to the same heart cycle sub-set as the moving average heart rate. Value Z may be 1.5 and the preceding heart rate may correspond to the heart cycle immediately preceding the specific heart cycle.

At least some of the embodiments further include the steps of using the heart rate to determine when the second Rpeak pulse at time t(2) is likely premature and when the second Rpeak pulse is likely premature, eliminating the second Rpeak pulse from the heart beat signal.

In some embodiments the step of using includes the step of determining when the second Rpeak pulse at time t(2) is likely premature and, when the second Rpeak pulse time is likely premature, eliminating the second Rpeak pulse from the heart beat signal. Here, where preceding cycles are heart cycles that precede the specific heart cycle, the step of using the heart rate to determine when the second Rpeak pulse time t(2) is likely premature may include the step of identifying a moving average rate corresponding to the moving average heart rate of a sub-set of the preceding cycles and determining that the second Rpeak pulse time is likely premature when the heart rate is greater than X % of the moving average rate.

The method may still further include the steps of, when a likely premature Rpeak pulse time is eliminated, determining if the eliminated pulse time was likely premature and, if the eliminated pulse was likely premature, storing an estimated Rpeak pulse time t(e) corresponding to the EKG signal after times t(1). Here, where the heart beat signal includes a third Rpeak pulse at time t(3) where the third pulse follows second pulse corresponding to the specific heart cycle, the step of determining if the eliminated pulse was likely premature may include identifying a heart rate corresponding to times t(1) and t(3) and determining that the eliminated pulse was likely premature when the heart rate is less than Y % of the moving average rate.

The method may include the step of identifying a moving average period corresponding to the moving average heart cycle period of a sub-set of the preceding cycles and the step of determining if the eliminated pulse was likely premature may further include the steps of identifying a preceding heart rate corresponding to at least one preceding heart cycle, identifying the estimated R-peak time t(e) as the time that precedes time t(3) by the moving average period, identifying an estimated heart rate corresponding to times t(e) and t(1) and determining that the eliminated pulse was likely premature when the estimated heart rate is less than Z times the preceding heart rate. The step of storing may include adding an R-peak pulse to the EKG signal.

The invention further includes an apparatus to be used with a CT imaging system including a heart beat monitor that senses R-peaks and generates a heart beat signal including R-peak pulses where each R-peak pulse indicates a sensed peak heart cycle magnitude, the method for correcting for heart beat signal errors corresponding to data collected over the course of several heart cycles, the apparatus comprising a processor running a pulse sequencing program to perform the steps of, for each specific heart cycle where the specific heart cycle corresponds to a period between first and second R-peak pulses occurring at times t(1) and t(2), respectively, identifying a heart rate, using the heart rate to determine when an R-peak error has likely occurred and, when an R-peak error has likely occurred, modifying the heart beat signal to correct for the likely error.

In some embodiments the program causes the processor to perform the step of using by performing the step of determining when at least one undetected R-peak pulse has likely occurred between times t(1) and t(2) and to perform the step of modifying by, when at least one undetected R-peak has likely occurred, inserting at least one estimated R-peak pulse into the heart beat signal at an estimated time t(e) between times t(1) and t(2). More specifically, where the preceding cycles are heart cycles that precede the specific heart cycle, the program may cause the processor to perform the step of using by further performing the steps of identifying a moving average rate corresponding to the moving average heart rate of a sub-set of the preceding cycles and determining that at least one undetected R-peak pulse has likely occurred between times t(1) and t(2) when the heart rate is less than Y % of the moving average rate.

The program may also cause the processor to further perform the step of identifying a moving average period corresponding to the moving average heart cycle period of a sub-set of the preceding cycles and may cause the processor to perform the step of determining by further performing the steps of identifying a preceding heart rate corresponding to at least one preceding heart cycle, identifying the estimated R-peak time t(e) as the time that precedes time t(2) by the moving average period, identifying an estimated heart rate corresponding to times t(e) and t(1) and determining that at least one undetected R-peak pulse has likely occurred between times t(1) and t(2) when the estimated heart rate is less than Z times the preceding heart rate.

The processor may further use the heart rate to determine when the second Rpeak pulse at time t(2) is likely premature and, when the second Rpeak pulse time is likely premature, eliminate the second Rpeak pulse from the heart beat signal.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF DRAWINGS

FIG. 6 is a flow chart illustrating one method for identifying missing Rpeak pulses within an EKG signal and correcting for such missing pulses; and FIG. 7 is similar to FIG. 6, albeit illustrating one method for identifying artificial Rpeak pulses in an EKG signal and correcting for such artificial pulses.

DETAILED DESCRIPTION

Figure 1:
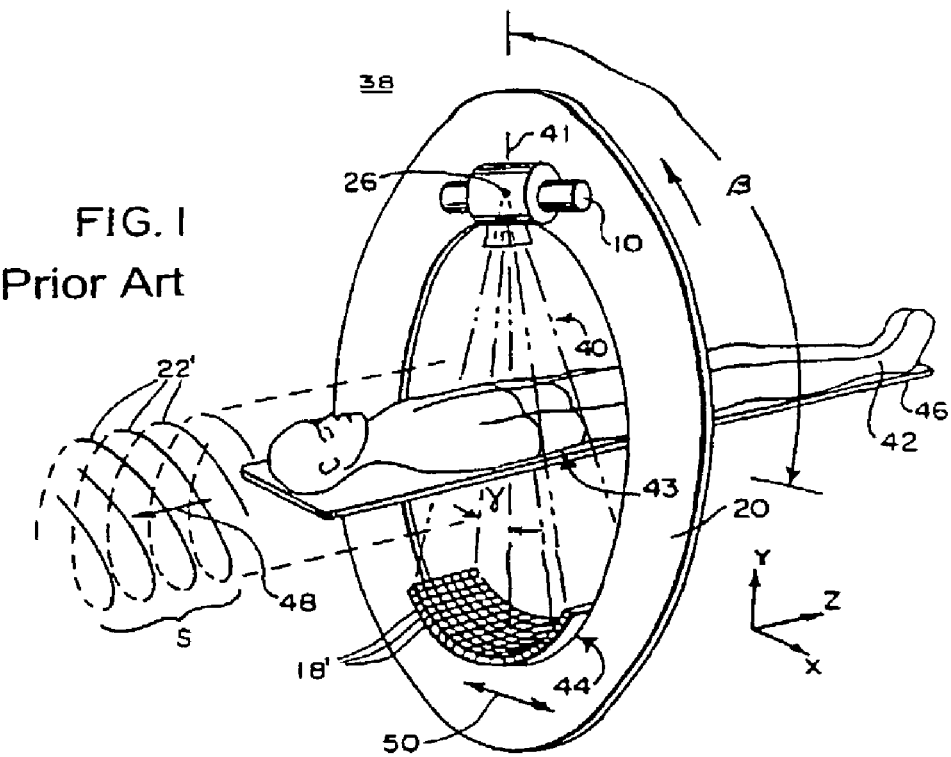
FIG. 1 is a perspective view of a CT apparatus used to practice the present invention which includes a detector array having rows and columns of detector elements and fan beam source.

A. Hardware: Referring now to FIG. 1, a CT scanner for use with the present invention includes a gantry 20 having an opening that defines an imaging area (not separately numbered) where gantry 20 supports an x-ray source 10 oriented to project a fan beam 40 of x-rays along a beam axis 41 through a patient 42 to an opposed detector array 44. The gantry 20 rotates to swing the beam axis 41 within a gantry plane 38 defining the x-y plane of a Cartesian coordinate system. Rotation of gantry 20 is measured by beam angle B from an arbitrary reference position within the gantry plane 38.

A patient 42 resets on a patient support table 46 which may be moved along a translation axis 48 aligned with a Z-axis of the Cartesian coordinate system. Table 46 crosses gantry plane 38 and is radio-translucent so as not to interfere with the imaging process.

The x-rays of the fan beam 40 diverge from the beam axis 41 within the gantry plane 38 across a transverse axis 50 generally orthogonal to both the beam axis 41 and the translation axis 48 at a fan beam angle γ. The x-rays of beam 40 also diverge slightly from the beam axis 41 and the gantry plane 38 across the translation axis 48 (i.e., along the Z axis).

After passing through patient 42, the x-rays of the fan beam 40 are received by detector array 44 which has detector elements 18' arranged in eight rows extending along the traverse axis 50 and a plurality of columns extending along the translation axis 48. The surface of detector array 44 may be planar or may follow a section of a sphere or cylinder having a center at focal spot 26 or alternatively at the system isocenter.

The detector elements 18' each receive x-rays and provide intensity measurements along separate rays of the fan beam 40. Each intensity measurement describes the attenuation via a line integral of one fan beam ray passing through a portion of volume or region of interest (ROI) 43 of patient 42. ROI 43 is typically wider along the Z-axis than the slice volume measured by a conventional CT system fan beam along the Z-axis. The rows of detector elements 18' subdivide the detector array and hence the fan beam along the Z-axis.

Figure 2:
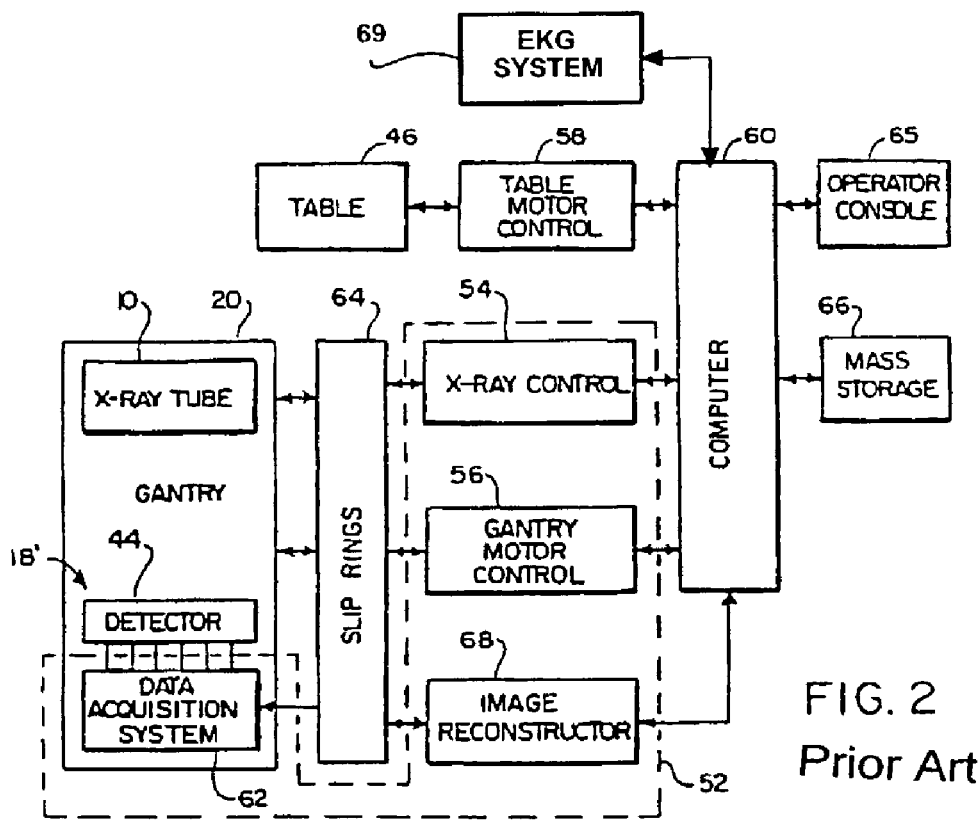
FIG. 2 is a block diagram of CT control system which may be used to control the CT apparatus of FIG. 1 and which is useful for the purposes of practicing the present invention.

Referring now to FIG. 2, an exemplary control system for controlling the CT imaging system of FIG. 1 includes a plurality of gantry associated control modules 52, a table motor control 58, a computer 60, an operator's console 65, a mass storage device 66 and an EKG system 69. The gantry associated control modules 52 include an x-ray control module 54, a gantry motor control module 56, a data acquisition system 62 and an image reconstructor 68. The x-ray control 54 provides power and timing signals to the x-ray source 10 to turn the source on and off as required under the control of computer 60. The gantry motor control 56 controls the rotational speed and position of the gantry 20 and provides information to computer 60 regarding gantry position. The table motor control 58 controls translation speed of table 46 and provides position feedback information back to computer 60.

Data acquisition system 62 samples and digitizes intensity signals from the detector elements 18' of detector array 44 and provides the digitized signals to computer 60 which in turn stores the signals in mass storage device 66. A slip ring connects all gantry mounted elements to other system components that are not mounted to the gantry for two way communication as well known in the art. After data is collected, image reconstructor 52 is controlled to combine the collected data to form images for display via console 65 or some other display device.

Referring still to FIGS. 1 and 2, computer 60 runs a pulse sequencing program to perform the inventive data processing method as described in more detail below. To this end, computer 60 receives commands and scanning parameters via operator console 65 which is generally a CRT display and keyboard. Console 65 allows an operator to enter parameters for controlling a data acquiring scan, to select images to be displayed and to display reconstructed image and other information from computer 60. A mass storage device or memory 66 provides a means for storing operating programs for the CT imaging system, as well as image data for future reference by the operator. Both computer 60 and image reconstructor 52 have associated electronic memory (not shown) for storing data.

Figure 3:
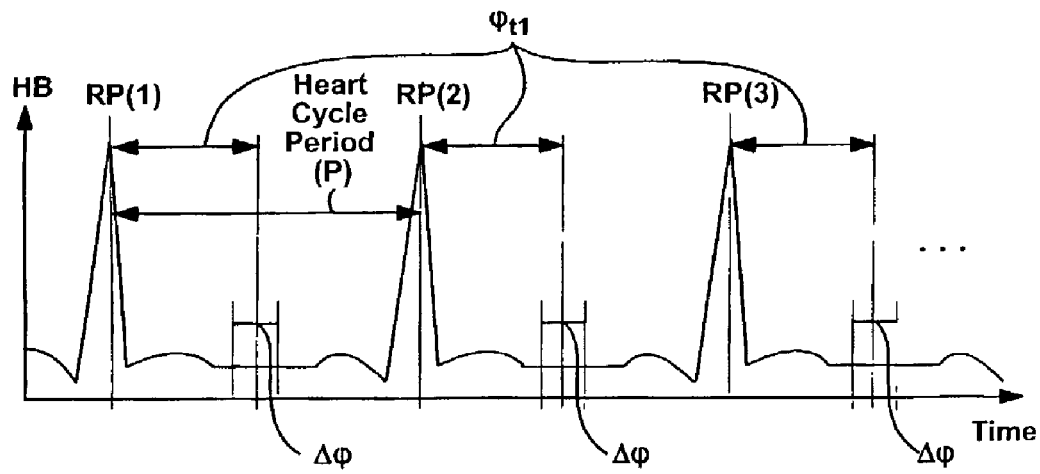
FIG. 3 is a graph illustrating an exemplary heart beating or EKG signal.

Referring still to FIG. 2, EKG system 69 includes sensors (not separately illustrated) that are linked to patient 42 and track the patient's heart beat as well known in the art. An exemplary heart beat is illustrated in FIG. 3 and includes a series of heart beat cycles having periods separated by peak pulses referred to as Rpeaks RP(1), RP(2), RP(3), etc., each Rpeak pulse, followed by a diastolic period during which the heart is relatively at rest as the heart chambers fill with blood to be pumped during the following heart beat. System 69 is linked to computer 60.

In operation, gantry motor control 56 brings gantry 20 up to a rotational speed and table motor control 58 begins translation of the table 46. The x-ray control 54 turns on the x-ray source 10 and projection data is acquired on the continuous basis as the table is moved through, and the gantry 20 is rotated about, the imaging area. At each beam angle B, the projection data acquired comprises intensity signals corresponding to each detector element 18' at each particular column and row of array 44.

During data acquisition, the data is correlated with heart beat phase information from the EKG system 69 and stored as helical data in mass storage device 66 and can be weighted and filtered to generate slice image data corresponding to separate trans-axial slice images through the ROI 43 using any of various processes well known in the art. The correlation process generally identifies data phase as a percent of the period between consecutive Rpeak pulse times. For instance, referring again to FIG. 3, data collected at a phase $\phi_{t1}$ corresponding to 65% of the period between Rpeaks RP(1) and RP(2) is correlated with phase angle $\phi_{t1}$.

Data corresponding to other phase angles between Rpeaks RP(1) and RP(2) is correlated and stored in a similar fashion.

Referring still to FIGS. 2 and 3, after data has been acquired, correlated with EKG signal phase and stored, a system operator may use console 65 to select a specific heart cycle phase angle for which to generate images and the number of images that are to be generated (i.e., required images). For instance, in FIG. 3, a user may request that 70 separate images be generated for ROI 43 and may select angle $\phi_{t1}$ as the heart cycle phase angle at which to generate the 70 required images. Again, phase angle is selected as a percentage of the total period between two consecutive Rpeak pulses (e.g., pulses RP(1) and RP(2)).

Once the number of required images and the phase angle is selected, computer 60 converts the selected phase angle into a phase range $\Delta\phi$ centered on the selected phase angle. For instance, in FIG. 3, where phase angle $\phi_{t1}$ is selected, computer 60 may automatically select range $\Delta\phi$. Range $\Delta\phi$ is typically manually adjustable using console 65. Next, computer 60 selects a subset of data from storage device 66 corresponding to the ROI 43 where the subset includes data from each heart cycle that is correlated with selected phase range $\Delta\phi$, filters the subset of data and back projects the subset to generate the required images.

B. Assumptions

Referring now to FIGS. 1 and 3, for the purposes of this explanation, it will be assumed that ROI 43 includes patient 42's heart characterized by a heart beat corresponding to the EKG signal waveform in FIG. 3 that has a typical 0.5 second cycle period P between consecutive Rpeaks (e.g., RP(1) and RP(2)). In addition, it will be assumed that helically acquired data is stored in its raw helical format initially and is only converted to slice image data after a system operator selects the heart cycle phase angle at which to generate images.

Moreover, it will be assumed that, while the diastolic phase range includes most of the phase between consecutive Rpeaks (e.g., Rpeaks RP(1) and RP(2)), enough data is collected during a shorter phase range to generate required images. For instance, referring still to FIG. 3, during phase range $\Delta\phi$, data sufficient to generate required slice images is acquired.

C. Theory: It has been recognized that when a patient 42 is at rest, the patient's heart beat signal is typically repetitive and periodic. Thus, for instance, where a patient's heart beat cycles comprise half-second intervals over the course of a plurality of consecutive heart beat cycles, it is likely that the next occurring cycle with have a period of approximately one-half second. Because of the cyclic and repetitive nature of a patient's heart beat cycle period, when an EKG signal is obtained corresponding to the patient's heart beat cycle, any appreciable deviation from a moving average cycle period indicates a likely error in the EKG signal. For instance, where an EKG signal includes first through tenth consecutive Rpeak pulses where each two consecutive Rpeak pulses are separated by one-half second, if the period between the $10^{th}$ and an $11^{th}$ Rpeak pulses is 1 second, it is very likely that a heart beat Rpeak pulse that occurred between the $10^{th}$ and $11^{th}$ Rpeak signals was either not detected or, if detected, was not recorded as part of the EKG signal. Similarly, where the moving average period between consecutive EKG signal Rpeak pulses is one-half second for $1^{st}$ through $10^{th}$ Rpeak pulses and the period between the $10^{th}$ and an $11^{th}$ Rpeak pulse is 1.5 seconds, it is likely that two heart beat Rpeak pulses were either undetected by the EKG system or simply were not recorded as part of the EKG signal.

Moreover, once again assuming a one-half second moving average period between EKG signal Rpeak pulses between $1^{st}$ through $10^{th}$ Rpeak pulses, if the period between the $10^{th}$ and an $11^{th}$ Rpeak pulse is 0.25 seconds and the period between the $11^{th}$ Rpeak pulse and a $12^{th}$ Rpeak pulse is also 0.25 seconds, it is very likely that the $11^{th}$ Rpeak pulse is artificial (i.e., is not associated with a n actual heart beat).

Furthermore, assuming a moving average cycle period between consecutive EKG signal Rpeak pulses of one-half second for $1^{st}$ through $10^{th}$ Rpeak pulses, if the period between the $10^{th}$ Rpeak pulse and an $11^{th}$ Rpeak pulse is 0.25 seconds and the period between the $11^{th}$ Rpeak pulse and a $12^{th}$ Rpeak pulse is 0.75 seconds, it is likely that the $11^{th}$ Rpeak pulse, if not artificial, was at least inadvertently shifted toward the $10^{th}$ Rpeak pulse and should have actually been recorded as having occurred between the $10^{th}$ and $12^{th}$ Rpeak pulses one-half second after the $10^{th}$ Rpeak pulse.

In each of the above cases, the EKG signal errors have been known to cause image artifacts and thereby reduce the diagnostic usefulness of resulting images. For this reason, the present invention has been developed to correct an EKG signal by either eliminating artificial Rpeak pulses, adding Rpeak pulses where Rpeak pulses likely occurred and were not recorded or, effectively, shifting registered Rpeak pulses when it is likely that one or more Rpeak pulses have inadvertently been shifted in the EKG signal.

Figure 4:
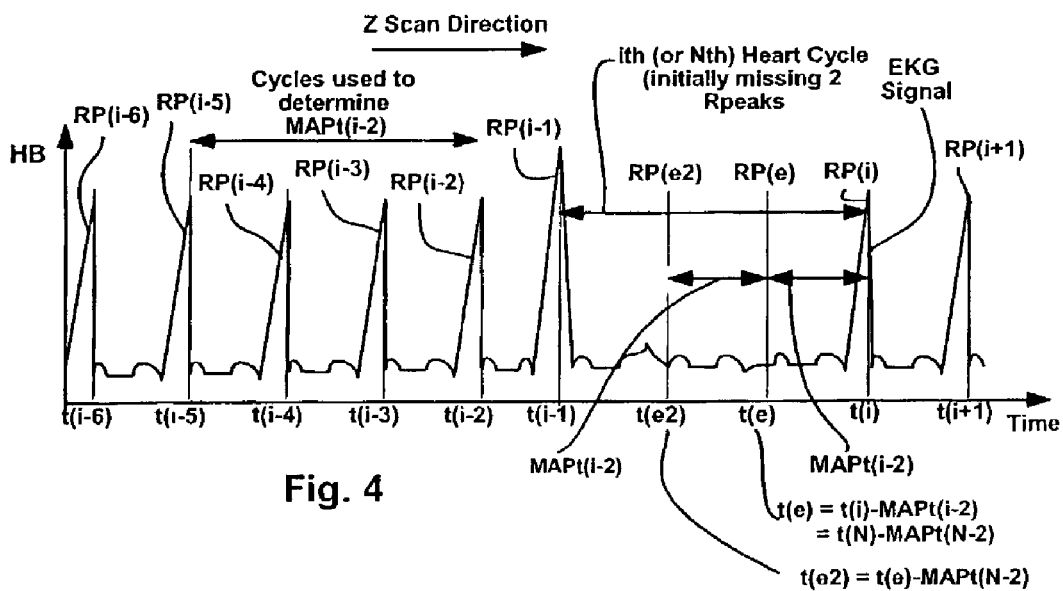
FIG. 4 is similar to FIG. 3, albeit illustrating an irregular EKG signal that is missing an Rpeak pulse.

Referring now to FIG. 4, an exemplary EKG signal including Rpeak pulses RP(i−6) through RP(i+1) is illustrated where the average signal cycle is 0.5 seconds. The exemplary EKG signal includes one exceptionally long signal cycle between Rpeak pulses RP(i−1) and RP(i). As illustrated, the long cycle is approximately three times as long (e.g., 1.5 seconds) as the cycles that precede the long cycle. Consistent with the discussion above, the exceptionally long signal cycle likely indicates one or more missed Rpeak pulses.

Referring still to FIG. 4, although more difficult to see, the cycle between Rpeak pulses RP(i−2) and RP(i−1) that immediately precedes the exceptionally long period between pulses RP(i−1) and RP(i) is shorter than the preceding cycles (e.g., the cycle between RP(i−3) and RP(i−2)). This phenomenon, where an Rpeak error (e.g., a missed pulse) is preceded by an irregular cycle, is often observed. For this reason, in at least some embodiments of the present invention, when moving average values are identified for comparison to values for a cycle being examined (CBE), the cycle immediately preceding the CBE is not included in the moving average calculations. For instance, where the CBE is the cycle ending with Rpeak pulse RP(i), the cycle immediately preceding the CBE (i.e., the cycle ending with Rpeak pulse RP(i−1) in FIG. 4) is ignored in the moving average calculations.

In the embodiment described here, moving average values are determined over three consecutive EKG signal cycles. For instance, referring yet again to FIG. 4, at a time t(i−2), the moving average values are determined for the three cycles between times t(i−5) and t(i−2). Other methods for determining moving average values are contemplated.

To explain an exemplary embodiment of the invention, it is helpful to provide a handful of definitions. To this end, t(i) will represent the time in milliseconds relative to the beginning of a cardiac helical scan of the Rpeak pulse at the end of the ith heart cycle detected by the EKG system 69. In this case, the following equations can be defined:

$$HRt(i) = \frac{1000*60}{t(i) - t(i-1)} \qquad \text{Eq. 1}$$

$$MAPt(i) = \frac{t(i) - t(i-3)}{3} \qquad \text{Eq. 2}$$

$$MAHRt(i) = \frac{1000*60}{MAPt(i)} \qquad \text{Eq. 3}$$

where HRt(i) is the heart rate of the ith heart cycle in beats per minute, MAPt(i) represents the three sample moving average of the heart cycle period for the ith heart cycle in milliseconds and MAHRt(i) represents the three sample moving average heart rate at the ith heart cycle in beats per minute. In addition, a cycle being examined (CBE) will be referenced herein as the Nth cycle.

Assuming the above convention, the process of correcting an EKG signal to compensate for missing Rpeak pulses devolves into two sub-processes including a missing Rpeak detection sub-process and a missing Rpeak correction sub-process. Algorithms for accomplishing each of the detection and correction sub-processes are described below. Nevertheless, it should be appreciated that the present invention contemplates other detection and/or correction algorithms. With respect to missing Rpeak detection, in the exemplary embodiment, beginning with the fifth EKG signal cycle, as the CBE (i.e., N=5), a processor inside computer 60 solves and examines the following equations to compare a moving average heart rate to the Nth heart rate:

$$MAP(N-2) = \frac{t(N-2) - t(N-5)}{3} \qquad \text{Eq. 4}$$

$$MAHR(N-2) = \frac{1000*60}{MAP(N-2)} \qquad \text{Eq. 5}$$

$$HRt(N) < Y*(MAHR)t(N-2) \text{ for } N > 4 \qquad \text{Eq. 6}$$

where Y is a fraction between 0 and 0.8 and, in the exemplary embodiment is approximately 0.55. Note that the process begins with the fifth heart cycle (i.e., N=5) so that moving averages corresponding to preceding cycles can be generated. Here, where Equation 6 is true, it is likely that one or more heart beats that actually occurred during the CBE failed to be recorded in the EKG signal and therefore one or more Rpeak pulses should be added to the EKG signal.

With respect to the missed Rpeak pulse correction sub-process, to estimate the phase or time location of the missed Rpeak pulse during the CBE, many different algorithms can be used. According to at least one relatively useful algorithm, the processor estimates the time location of the missed Rpeak pulse using the moving average cycle period MAP(N-2) identified by solving Equation 4 above. To this end, beginning at time t(N), the processor steps back one moving average period (MAP(N-2) at a time to identify progressively earlier potential missing Rpeak pulse times or estimated Rpeak pulse times t(e). Thereafter, the estimated time t(e) is used in conjunction with the time t(N-1) corresponding to the EKG signal Rpeak pulse at the beginning of the Nth or CBE cycle to generate an estimated heart rate HRt(e) that would result from insertion of an Rpeak pulse at time t(e). This is accomplished by solving Equation 1 with estimated time t(e) and time t(N+1) substituted for times t(i) and t(i−1), respectively. Next, the processor solves and examines the following equation:

$$HRt(e) < Z*HRt(N-1) \qquad \text{Eq. 7}$$

where Z is a multiplier factor which is typically greater than 1 and, in the exemplary embodiment will be approximately 1.5 and HRt(N−1) is the heart rate corresponding to the cycle that precedes the CBE in the original EKG signal.

Where Equation 7 is true, an Rpeak pulse is added to the EKG signal at the estimated time t(e). In FIG. 4, an added Rpeak pulse would be provided at time t(e).

Continuing, where a pulse is added at time t(e), the processor next identifies a second potential missing or estimated Rpeak pulse time t(e2) (see FIG. 4) by subtracting the moving average period MAP(N−2) from the first estimated Rpeak pulse time t(e) and then using the second estimated Rpeak pulse time t(e2) and the immediately preceding pulse time t(N−1) from the EKG signal to identify a second heart rate estimate HRt(e2). Thereafter, Equation 7 is solved and examined again using the second heart rate estimate HRt(e2) and, if Equation 7 is again true, another Rpeak pulse is inserted into the EKG signal at time t(e2).

To this end, referring still to FIG. 4, even after a pulse is added at estimated time t(e), the cycle between times t(e) and t(i−1) (i.e., t(N−1) in the present example) will be much longer (e.g., approximately twice as long) than the moving average MAPt(N−2) and therefore a second Rpeak pulse would be inserted in the EKG signal at time t(e2).

This process of identifying earlier estimated Rpeak pulse times and corresponding estimated heart rate values and solving and examining the results of Equation 7 is repeated until Equation 7 is false at which point the missing Rpeak correction sub-process is complete for the CBE. Continuing, the detection and correction sub-processes above are performed on every EKG signal cycle after the $4^{th}$ cycle.

In addition, to ensure that all acquired scan data can be used for imaging purposes at the end of the EKG signal where the last recorded Rpeak is RP(N) at time t(N), additional Rpeak pulse time stamps are added at MAP(N−2) intervals after time t(N) until the EKG signal includes at least one Rpeak pulse time beyond the end of the scan. This process of adding Rpeak times at the end of the EKG signal ensures that if the EKG system is turned off prior to the end of the scan or if EKG signal recording problems occur at the end of a scan, the scan data can still be correlated with cardiac phase and used for imaging purposes.

Figure 5:
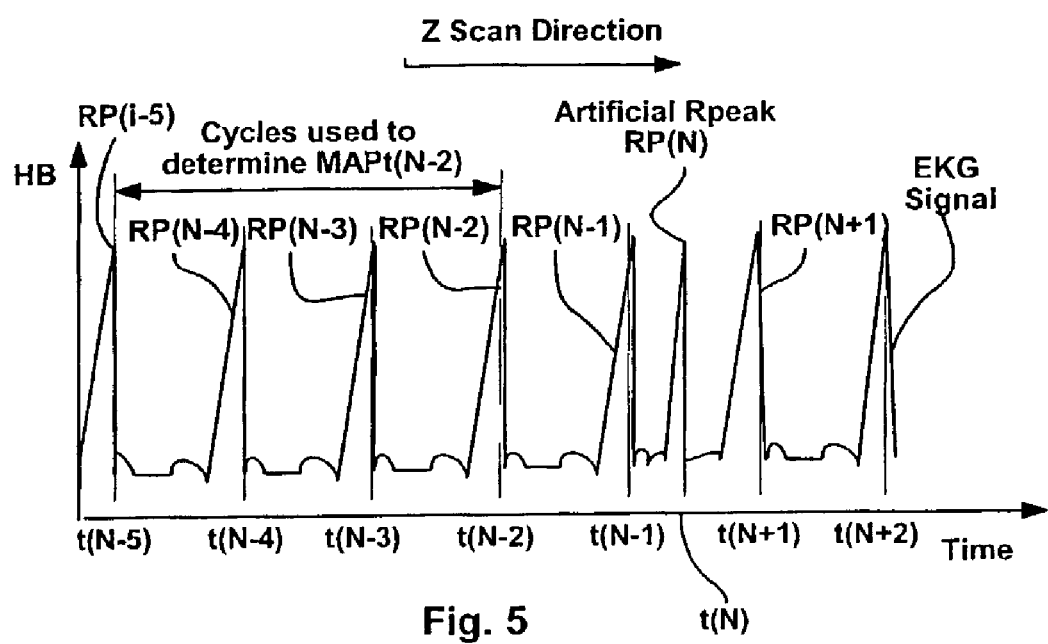
FIG. 5 is similar to FIG. 4, albeit illustrating an EKG signal including an artificial Rpeak pulse.

Referring now to FIG. 5, a process similar to the process described above is used to determine when a likely artificial Rpeak has incorrectly been recorded in an EKG signal. In FIG. 5, as in FIG. 4, a moving average period and a moving average heart rate with respect to a CBE N ending with pulse RP(N) at time t(N) are identified by solving Equations 4 and 5 above. In addition, a heart rate HRt(N) corresponding to the CBE is identified by solving Equation 1. Next, the processor solves and examines the following equation:

$$HRt(N) > X*MAHR(N-z) \qquad \text{Eq. 8}$$

where X is greater than 1.0 and, in the exemplary embodiment, is approximately 1.5. Where Equation 8 is true, the Rpeak pulse RP(N) is likely either premature or artificial and in either case should be removed.

Next, after a likely premature or artificial Rpeak pulse has been removed from the EKG signal, the process described above for identifying premature or artificial Rpeak pulses is repeated for the next Rpeak pulse in the EKG signal until Equation 8 is false. Where at least one Rpeak pulse is removed from between a preceding Rpeak pulse and a following Rpeak pulse, when Equation 8 is eventually false, prior to moving onto the next cycle to be examined, in at least one embodiment, the processor performs the missing detection and correction process described above with the cycle between the preceding and following Rpeak pulses (i.e., the cycle between the Rpeak pulses that are before and after the removed Rpeak pulses) as the CBE. By following up removal of an Rpeak pulse with the missing detection/correction process, if the removed Rpeak pulse was simply premature as opposed to artificial, a likely correct Rpeak pulse will be reinserted in the EKG signal thereby effectively shifting the premature pulse in an ideal fashion.

For example, referring still to FIG. 5, assuming the periods between times t(N−1) to t(N) and t(N) to t(N+1) are 0.25 and 0.75 seconds, respectively, and that the moving average period MAP(N−2) is 0.5 seconds, it is likely pulse RP(N) is premature by 0.25 seconds instead of artificial. In this case the artificial/premature process described above would first remove pulse RP(N) from the signal. Thereafter the missing pulse detection/correction process would insert an Rpeak pulse 0.5 seconds (i.e., the MAPt(N−2)) after pulse RP(N−1) to, in effect, shift the premature pulse to an ideal time and phase location.

C. Operation: Referring now to FIG. 6, one method 98 for identifying likely missing Rpeak pulses within an EKG signal and for correcting for likely missed Rpeak pulses is illustrated. Referring also to FIGS. 1, 2 and 4, at block 102, system 38 is used to acquire CT data and an EKG heart beat signal correlate the CT data and EKG signal and store the correlated data and signals. At block 100 two separate counters N and M are set equal to 5 and 1, respectively. At block 104, starting with the fifth EKG signal cycle (i.e., N=5) as the CBE, the heart rate for the CBE is identified along with heart rate HRt(N−1), the moving average period MAPt(N−2) and the moving average heart rate MAHRt(N−2). Next, at block 106, the processor solves Equation 6.

Where Equation 6 is false, control passes to block 108 where counter N is incremented by 1 and control passes back up to block 104. Thus, where the heart rate corresponding to a CBE is similar to the moving average heart rate MAHRt(N−2), the processor is programmed to determine that no Rpeak pulses have been missed during the CBE.

Where Equation 6 is true and an Rpeak pulse has likely been missed, control passes to block 110 where the processor estimates the time and generates an estimated Rpeak pulse time t(e) corresponding to a likely missed pulse by stepping back MAPt(N−2) from time t(N). Control then passes to block 112 where the processor identifies the estimated heart rate HRt(e) corresponding to a cycle defined by estimated time t(e) and the preceding Rpeak pulse time t(N−1). At block 114 the estimated heart rate HRt(e) is plugged in to Equation 7 and the processor examines the result. Where Equation 7 is false, no Rpeak pulses should be added to the EKG signal and control passes to block 116 where counter M is reset to 1. Thereafter control passes again back up to block 108 where counter N is incremented by 1 prior to control passing to block 102 to cause the processor to repeat the process for the next signal cycle (i.e., where N=6).

Referring again to block 114, where Equation 7 is true, control passes to block 118 where the processor inserts an Rpeak pulse at time t(e). Next, control passes to block 120 where the time variable t(N) is set equal to time t(e). Thereafter, control passes to block 122 where counter M is incremented by 1 and then loops back up to block 110 where the processor determines whether or not a second Rpeak pulse was likely missed during the CBE. The looping process through blocks 110, 112, 114, 118, 120 and 122 continues for each likely missed Rpeak pulse until Equation 7 at block 114 is false and control passes to block 116.

Referring now to FIG. 7, one inventive method 99 for determining when an artificial or premature Rpeak pulse has occurred in an EKG signal and for correcting the signal is illustrated. Referring also and once again to FIGS. 1, 2 and 5, at block 126, the CT data is acquired and correlated with the EKG heart beat signal and is then stored. At block 124, counters N and M are set equal to 5 and 1, respectively. At block 128, starting with the fifth Rpeak pulse, the processor determines heart rate HRt(N), the heart rate HRt(N−1), the moving average period MAPt(N−2) and the moving average heart rate MAHRt(N−2). At block 130, the processor solves Equation 8 and examines the result. If Equation 8 is false, control passes to block 132 where counter N is incremented by 1 and control again passes back up to block 128. Where Equation 8 is true, control passes to block 134 where the pulse RP(N) at time t(N) is eliminated. Next, control passes to the loop beginning at block 138 and continuing through block 150 which is essentially identical to the loop of FIG. 6 which begins at block 110 and continues through block 122. Generally, the block 138 through 150 loop is used to determine whether or not the eliminated Rpeak pulse was artificial or simply premature. To this end, the loop including blocks 138 through 150, in general, identifies where, between preceding and following Rpeak pulses RP(N−1) and RP(N+1), respectively, a missing Rpeak pulse may occur and then determines if, assuming the missing pulse were added to the EKG signal, the resulting heart rate would exceed a likely heart rate.

To this end, at block 138, the processor generates an Rpeak peak estimated time t(e) at time t(N+1)−MAPt(N−2) and then at block 140 identifies an estimated heart rate HRt(e) corresponding to times t(e) and t(N−1). At block 142 the processor solves Equation 7 and then examines the result. If Equation 7 is false and no Rpeak pulse should be added, control passes to block 144 where counter M is set equal to 1 and control again passes back up to block 132. However, where Equation 7 is true, control passes to block 146 where the estimated Rpeak pulse is added to the EKG signal at time t(e). Again, as in FIG. 6, control passes to block 148 where time value t(N) is set equal to time t(e). Thereafter, control passes to block 150 where counter M is incremented by 1 and then control passes back up to block 138 again.

It should be understood that the methods and apparatuses described above are only exemplary and do not limit the scope of the invention, and that various modifications could be made by those skilled in the art that would fall under the scope of the invention. For example, while the methods for detecting/correcting for missing Rpeak pulses and for detecting/correcting for artificial or premature pulses are described as separate methods, it should be appreciated that a combination of methods for accomplishing all of the tasks may be performed sequentially for each EKG signal cycle prior to moving on to subsequent signal cycles. In addition, while certain numbers have been identified above for the variables in various equations, other numbers are contemplated and, in fact, many other equations and algorithms may be substituted for the equations described. Moreover, while the invention is described as one wherein Rpeak pulses are added to an EKG signal, in reality, all that is actually used from the EKG signal are the Rpeak pulse times and therefore, instead of inserting Rpeak pulses into the EKG signal, the correction process may simply identify time stamps of Rpeak pulses and remove time stamps corresponding to artificial and/or premature Rpeak pulses.

To apprise the public of the scope of this invention, the following claims are made:

1. A method to be used with a CT imaging system including a heart beat monitor that senses R-peaks and generates a heart beat signal including R-peak pulses where each R-peak pulse indicates a sensed peak heart cycle magnitude, the method for correcting for heart beat signal errors corresponding to data collected over the course of several heart cycles, the method comprising the steps of:

for each specific heart cycle where the specific heart cycle corresponds to a period between first and second R-peak pulses occurring at times t(1) and t(2), respectively:

identifying a heart rate;

using the heart rate to determine when an R-peak error has likely occurred; and when an R-peak error has likely occurred, modifying the heart beat signal Rpeak pulse times by at least one of storing and eliminating at least one R-peak pulses;

wherein the step of using includes the step of determining when at least one undetected R-peak has likely occurred between times t(1) and t(2) and where the step of modifying includes, when at least one undetected R-peak has likely occurred, storing at least one estimated R-peak pulse time t(e) corresponding to the heart beat signal between times t(1) and t(2).

2. The method of claim 1 wherein preceding cycles are heart cycles that precede the specific heart cycle and the step of using further includes the steps of identifying a moving average rate corresponding to the moving average heart rate of a sub-set of the preceding cycles and determining that at least one undetected R-peak pulse has likely occurred between times t(1) and t(2) when the heart rate is less than Y % of the moving average rate.

3. The method of claim 2 further including the step of identifying a moving average period corresponding to the moving average heart cycle period of a sub-set of the preceding cycles and wherein the step of determining further includes the steps of identifying a preceding heart rate corresponding to at least one preceding heart cycle, identifying the estimated R-peak time t(e) as the time that precedes time t(2) by the moving average period, identifying an estimated heart rate corresponding to times t(e) and t(1) and determining that at least one undetected R-peak pulse has likely occurred between times t(1) and t(2) when the estimated heart rate is less than Z times the preceding heart rate.

4. The method of claim 3 further including the step of:
(a) determining when at least another undetected R-peak has likely occurred between times t(1) and t(2); and
(b) when at least another undetected R-peak has likely occurred, storing another estimated R-peak pulse time corresponding to the heart beat signal between times t(e) and t(1).

5. The method of claim 4 further including the step of repeating steps (a) and (b) until it is unlikely that another undetected R-peak pulse has occurred between times t(1) and t(2).

6. The method of claim 4 wherein the step of determining when at least another undetected R-peak has likely occurred further includes the steps of identifying the next estimated R-peak time as the time that precedes the previous R-peak time corresponding to the most recently stored estimated R-peak pulse time by the moving average period, identifying an estimated heart rate corresponding to the next estimated and previous R-peak times and determining that at least another R-peak pulse has likely occurred between times t(1) and t(2) when the estimated heart rate is less than Z times the preceding heart rate.

7. The method of claim 3 wherein the moving average heart cycle period corresponds to the same heart cycle sub-set as the moving average heart rate.

8. The method of claim 3 wherein Z is 1.5 and the preceding heart rate corresponds to the heart cycle immediately preceding the specific heart cycle.

9. The method of claim 2 wherein the moving average rate is the average corresponding to the heart cycles that precede the specific heart cycle by four cycles, three cycles and two cycles and Y is 55.

10. The method of claim 1 further including the steps of:
using the heart rate to determine when the second Rpeak pulse at time t(2) is likely premature; and
when the second Rpeak pulse is likely premature, eliminating the second Rpeak pulse from the heart beat signal.

11. The method of claim 1 wherein the step of using includes the step of determining when the second Rpeak pulse at time t(2) is likely premature and, when the second Rpeak pulse time is likely premature, eliminating the second Rpeak pulse from the heart beat signal.

12. The method of claim 11 wherein preceding cycles are heart cycles that precede the specific heart cycle and, wherein, the step of using the heart rate to determine when the second Rpeak pulse time t(2) is likely premature includes the step of identifying a moving average rate corresponding to the moving average heart rate of a sub-set of the preceding cycles and determining that the second Rpeak pulse time is likely premature when the heart rate is greater than X % of the moving average rate.

13. The method of claim 12 further including the steps of, when a likely premature Rpeak pulse time is eliminated, determining if the eliminated pulse time was likely premature and, if the eliminated pulse was likely premature, storing an estimated Rpeak pulse time t(e) corresponding to the heart beat signal after times t(1).

14. The method of claim 13 wherein the heart beat signal includes a third Rpeak pulse at time t(3) where the third pulse follows second pulse corresponding to the specific heart cycle and, wherein, the step of determining if the eliminated pulse was likely premature includes identifying a heart rate corresponding to times t(1) and t(3) and determining that the eliminated pulse was likely premature when the heart rate is less than Y % of the moving average rate.

15. The method of claim 14 further including the step of identifying a moving average period corresponding to the moving average heart cycle period of a sub-set of the preceding cycles and wherein the step of determining if the eliminated pulse was likely premature further includes the steps of identifying a preceding heart rate corresponding to at least one preceding heart cycle, identifying the estimated R-peak time t(e) as the time that precedes time t(3) by the moving average period, identifying an estimated heart rate corresponding to times t(e) and t(1) and determining that the eliminated pulse was likely premature when the estimated heart rate is less than Z times the preceding heart rate.

16. The method of claim 1 wherein the step of storing includes adding an R-peak pulse to the heart beat signal.

17. A method to be used with a CT imaging system including a heart beat monitor and a data acquisition system, the acquisition system used to collect CT data during a period ending at a time t(end), the monitor sensing R-peaks and generating a heart beat signal including R-peak pulses where each R-peak pulse indicates a heart beat and the last Rpeak pulse occurs at time t(N), the method for correcting for heart beat signal errors corresponding to data collected over the course of several heart cycles, the method comprising the steps of:

determining when time t(N) precedes time t(end);

where time t(N) precedes time t(end), identifying a moving average heart cycle period corresponding to a sub-set of signal cycles that precede the cycle ending at time t(N);

adding additional Rpeak times to the end of the heart beat signal until the last additional time follows time t(end) where each additional time follows the preceding Rpeak time by the moving average.

18. The method of claim 17 wherein the period ending at time t(N) is an Nth cycle and the moving average period is determined by averaging the cycle periods for the $N-5^{th}$ through $N-2^{nd}$ cycles.

* * * * *